United States Patent
Lawandy

(10) Patent No.: US 10,354,471 B2
(45) Date of Patent: Jul. 16, 2019

(54) DEVICE AND METHOD FOR USING GASOCHROMIC SENSING FOR EVALUATING FITNESS

(71) Applicant: Spectra Systems Corp., Providence, RI (US)

(72) Inventor: Nabil M. Lawandy, Saunderstown, RI (US)

(73) Assignee: Spectra Systems Corporation, Providence, RI (US)

( * ) Notice: Subject to any disclaimer, the term of this patent is extended or adjusted under 35 U.S.C. 154(b) by 114 days.

(21) Appl. No.: 15/242,052

(22) Filed: Aug. 19, 2016

(65) Prior Publication Data

US 2017/0069155 A1  Mar. 9, 2017

Related U.S. Application Data

(60) Provisional application No. 62/245,724, filed on Oct. 23, 2015, provisional application No. 62/207,241, filed on Aug. 19, 2015.

(51) Int. Cl.
| | |
|---|---|
| *G01N 15/08* | (2006.01) |
| *G07D 7/185* | (2016.01) |
| *G07D 7/06* | (2006.01) |

(52) U.S. Cl.
CPC ........... *G07D 7/185* (2013.01); *G01N 15/082* (2013.01); *G07D 7/06* (2013.01)

(58) Field of Classification Search
CPC .................................................. G01N 15/082
(Continued)

(56) References Cited

U.S. PATENT DOCUMENTS

| | | |
|---|---|---|
| 5,193,854 A | 3/1993 | Borowski, Jr. et al. |
| 2005/0195391 A1 | 9/2005 | Alexander |

(Continued)

FOREIGN PATENT DOCUMENTS

| | | |
|---|---|---|
| WO | 2009133997 A1 | 11/2009 |
| WO | 2010055308 A1 | 5/2010 |
| WO | 2015066716 A2 | 5/2015 |

OTHER PUBLICATIONS

Written Opinion of the International Searching Authority in PCT/US2014/063940 (dated May 15, 2015).

(Continued)

*Primary Examiner* — Walter L Lindsay, Jr.
*Assistant Examiner* — Philipmarcus T Fadul
(74) *Attorney, Agent, or Firm* — Pryor Cashman LLP

(57) ABSTRACT

A method and apparatus for evaluating the fitness of an object based on determination of a measure of permeability of the object, including positioning the object between a fluid source and a gasochromic material, dispensing a fluid from the fluid source towards the object such that at least a portion of the fluid flows through the object and contacts the gasochromic material, exciting the gasochromic material with an excitation source such that an emission of the gasochromic material is in response to the excitation source and the fluid, detecting the emission from the gasochromic material to determine the permeability of the object, and evaluating the fitness of the object based on the determination of the permeability of the object. The gasochromic material may also be included in the object.

17 Claims, 10 Drawing Sheets

(58) Field of Classification Search
USPC .............................................................. 73/38
See application file for complete search history.

(56) References Cited

U.S. PATENT DOCUMENTS

| | | |
|---|---|---|
| 2007/0089489 A1 | 4/2007 | Lewnard et al. |
| 2008/0110243 A1 | 5/2008 | Burke et al. |
| 2011/0199222 A1* | 8/2011 | Lawandy .............. G01N 21/783 340/632 |
| 2013/0052745 A1* | 2/2013 | Brooker ................. G01N 21/78 436/164 |
| 2013/0287264 A1 | 10/2013 | Chen et al. |
| 2014/0050903 A1* | 2/2014 | Lettow ..................... H01B 1/24 428/201 |
| 2014/0116474 A1* | 5/2014 | Lawandy .............. B08B 7/0021 134/34 |
| 2014/0159860 A1 | 6/2014 | Lawandy |
| 2016/0178501 A1 | 6/2016 | Lawandy |

OTHER PUBLICATIONS

Search Report of the International Searching Authority in PCT/US2014/063940 (dated May 15, 2015).
Written Opinion of the International Searching Authority in PCT/US16/47835 (dated Dec. 15, 2016).

* cited by examiner

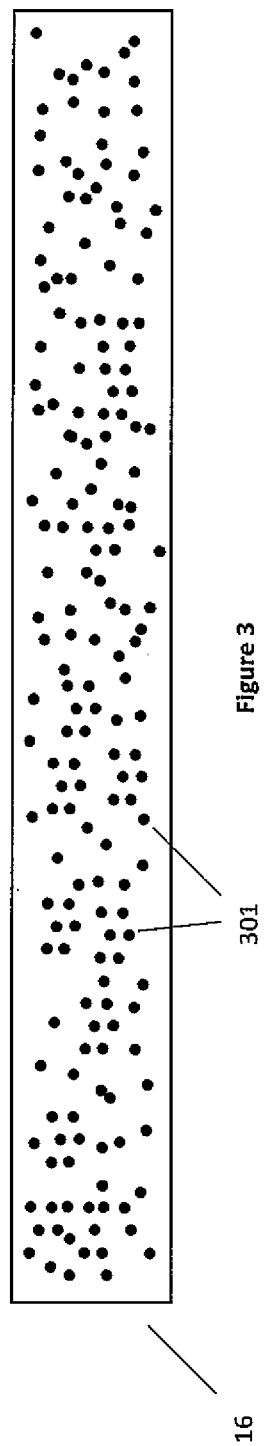

DEVICE AND METHOD FOR USING GASOCHROMIC SENSING FOR EVALUATING FITNESS

CROSS-REFERENCE TO RELATED APPLICATIONS

This application claims the benefit of U.S. Provisional Patent Application No. 62/207,241, filed Aug. 19, 2015, and U.S. Provisional Patent Application No. 62/245,724, filed Jan. 20, 2016, the entire disclosures of which are incorporated herein by reference.

TECHNICAL FIELD

The present invention relates generally to devices and methods for sensing the transmission of a gas or liquid through a material or membrane. More specifically, the present invention relates to the use of gasochromic materials to test the porosity or the permeability of an object, such as a secure instrument having a substrate, visual data, and a security feature, to evaluate the fitness of the object.

BACKGROUND OF THE INVENTION

High security documents such as banknotes and other paper stock have substrates formed from various materials, which may be porous materials such as pulp cotton fibers. Moreover, in the United States, paper currency is made from a non-woven combination of 75% cotton and 25% linen fibers. In most other countries, pulp-based substrates are used. Some countries, such as Canada, have used cotton and paper blended banknotes. In addition, countries such as Australia, New Zealand and Canada have issued banknotes having polymer substrates, e.g., substrates including biaxially oriented polypropylene. The substrate, which may include one or more plies of the substrate material, may include security features such as laminated polymer or paper security threads, planchettes, and watermarks formed directly into the substrate.

As counterfeiters have become more sophisticated, the security features in such documents have had to become more advanced as well in order to prevent widespread fraud. As the substrates of such secure documents have become more advanced, the cost to produce them has also increased, thus making the replacement of worn currency quite expensive. Therefore, it is important that in addition to being secure, such documents must have a high level of durability, lack certain imperfections, and be removed from circulation when the appropriate criteria on their fitness are available. In addition, the measurement and monitoring of porosity and permeability of various media during manufacturing is of importance to obtaining high quality products meeting the required quality.

Banknotes, lottery scratch tickets, and other documents are removed from circulation for a variety of reasons. For example, lottery scratch tickets may be removed if they have pinpricks in the coating. In addition, based on one study, 81% of banknotes are removed because of soiling, 9% are removed because of damage caused by mechanical means, especially tearing, 5% are removed because of graffiti on the notes, 4% are removed because of general wear and tear, and 1% are removed because of damage to the security elements.

Banknotes have a finite time in circulation due to soling and tearing of the notes in use by the public. For example, it takes about 4,000 double folds (first forward and then backward) before a U.S. paper bill will tear. Banknotes are handled in many ways during their usable life and experience a variety of mechanical stresses, as well as being brought into contact with substances that can dirty the notes, resulting in difficulty in their authentication and use.

One important parameter used to determine the fitness of banknotes is limpness. When banknotes have been in circulation, the mechanical wear from folds, handling, and use in bill acceptors, results in a loss of mechanical elasticity that leads to the notes becoming limp. In addition, the mechanical wear of banknotes results in banknotes being torn and/or ripped. This "limpness," tearing, and ripping has been shown to be directly related to changes in the porosity of the banknote with mechanical wear. In particular, the porosity of the banknotes increases with use and manifests itself in a lower effective elastic constant.

Permeability has been shown to have a correlation to limpness. Studies have also correlated permeability to deflection and stiffness. Permeability is sensitive to network deformation of a substrate, and changes in permeability, typically due to changes in porosity, can be an early indicator of the condition of the substrate network, which itself can be an early predictor of limpness. Existing methods for measuring permeability and porosity, however, are too slow for machine-readable fitness measurements.

Generally, porosity is an important physical parameter for a number of applications and as a diagnostic tool. For example, it plays a critical role in membrane separations, time released drug delivery, soil science and engineering and banknote fitness. In particular, porosity is used in a variety of fields including pharmaceuticals, ceramics, metallurgy, materials, manufacturing, earth sciences, soil mechanics, and engineering.

Typically, porosity and permeability are measured using the transport of liquids or gasses and characterizing the void fraction, physisorption, and tortuosity of the voids in a material or membrane. The detection of the gas or liquid passing through the material or membrane is measured with a variety of methods, including flow meters, mass spectrometers, absorption spectra, fluorescence, mercury intrusion, water evaporation, and mass change, computed tomography.

Specifically, with respect to banknotes, given the large numbers of banknotes in circulation for even small countries, determining the fitness of banknotes is not only of importance in cost control, but also poses a serious technical challenge in terms of processing speed and accuracy. As a result, accurate determination of the fitness of banknotes by measurement of permeability and porosity would be beneficial if it could be performed on the high speed sorters used by commercial and central banks to process currency for authenticity and fitness.

There is, therefore, a need to employ an efficient and accurate manner of identifying whether banknotes, lottery scratch tickets, or other documents are torn, ripped, have been tampered with and/or have been subject to excessive mechanical wear based on the porosity of the documents in order to determine whether the documents should remain in circulation or be destroyed.

SUMMARY OF THE INVENTION

It is an object of the present invention to provide an apparatus and method for testing the porosity or permeability of a material, membrane or other object, such as a secure instrument, banknote or lottery ticket, to evaluate the fitness of the object.

In general, in one aspect, the invention features a method of evaluating the fitness of an object based on determination of a measure of permeability of the object, including positioning the object between a fluid source and a gasochromic material, dispensing a fluid from the fluid source towards the object such that at least a portion of the fluid flows through the object and contacts the gasochromic material, exciting the gasochromic material with an excitation source such that an emission of the gasochromic material is in response to the excitation source and the fluid, detecting the emission from the gasochromic material to determine the permeability of the object, and evaluating the fitness of the object based on the determination of the permeability of the object.

Implementations of the invention may include one or more of the following features. Evaluating the fitness of the object may be determining presence of a tear in the object, determining limpness of the object or determining mechanical wear of the object. The fluid may be a gas rich in oxygen or containing substantially no oxygen. The gasochromic material may be coated on a substrate. The object may be a secure instrument including a substrate, visual data, and a security feature, which may be a banknote. The object may be a lottery scratch ticket comprising a scratch layer and a printed data layer. The method may further include advancing the object through a space between the fluid source and the gasochromic material.

In general, in another aspect, the invention features a method of evaluating the fitness of an object including a gasochromic material based on determination of a measure of permeability of the object, including dispensing a fluid from the fluid source towards the object such that at least a portion of the fluid flows through the object and contacts the gasochromic material, exciting the gasochromic material with an excitation source such that an emission of the gasochromic material is in response to the excitation source and the fluid, detecting the emission from the gasochromic material to determine the permeability of the object, and evaluating the fitness of the object based on the determination of the permeability of the object.

Implementations of the invention may include one or more of the following features. Evaluating the fitness of the object may be determining presence of a tear in the object, determining limpness of the object or determining mechanical wear of the object. The fluid may be a gas rich in oxygen or containing substantially no oxygen. The gasochromic material may be coated on the object, or the object may include a substrate doped with gasochromic moieties. The object may be a secure instrument including a substrate, visual data, and a security feature, which may be a banknote. The object may be a lottery scratch ticket including a scratch layer and a printed data layer. The method may further include advancing the object across the fluid source.

In general, in another aspect, the invention features an apparatus for evaluating the fitness of an object based on a determination of a measure of permeability of the object, including a gasochromic material, a fluid source for dispensing fluid towards the object disposed between the fluid source and the gasochromic material, an excitation source for exciting the gasochromic material such that an emission of the gasochromic material is in response to the excitation source and the fluid, and a detection device for detecting the emission of the gasochromic material to determine the permeability of the object for evaluating the fitness of the object.

Implementations of the invention may include one or more of the following features. The fluid may be a gas rich in oxygen or containing substantially no oxygen. The gasochromic material may be coated on a substrate. The object may be a secure instrument including a substrate, visual data, and a security feature, which may be a banknote. The object may be a lottery scratch ticket including a scratch layer and a printed data layer. The apparatus may further include a transport device for advancing the object through a space between the fluid source and the gasochromic material. The excitation source may be a light emitting diode, a laser or a lamp. The detection device may include photodiodes, photomultipliers or photovoltaic cells.

In general, in another aspect, the invention features an apparatus for evaluating the fitness of an object including a gasochromic material based on determination of a measure of permeability of the object, including a fluid source for dispensing fluid towards the object, an excitation source for exciting the gasochromic material such that an emission of the gasochromic material is in response to the excitation source and the fluid, and a detection device for detecting the emission of the gasochromic material to determine the permeability of the object for evaluating the fitness of the object.

Implementations of the invention may include one or more of the following features. The fluid may be a gas rich in oxygen or containing substantially no oxygen. The gasochromic material may be coated on the object, or the object may include a substrate doped with gasochromic moieties. The object may be a secure instrument including a substrate, visual data, and a security feature, which may be a banknote. The object may be a lottery scratch ticket comprising a scratch layer and a printed data layer. The apparatus may further include a transport device for advancing the object across the fluid source. The excitation source may be a light emitting diode, a laser or a lamp. The detection device may include photodiodes, photomultipliers or photovoltaic cells.

BRIEF DESCRIPTION OF THE DRAWINGS

The above-mentioned and other aspects, features and advantages can be more readily understood from the following detailed description with reference to the accompanying drawings, wherein:

FIG. 3 is a diagram of a substrate with embedded gasochromic materials according to an embodiment of the present disclosure;

DETAILED DESCRIPTION OF THE PREFERRED EMBODIMENTS

The present invention provides for apparatus and methods for sensing the transmission of a gas or liquid through an object, material, or membrane. More specifically, the present invention provides for methods and apparatus for measuring the porosity and/or the permeability of secure instruments, such as banknotes and lottery scratch tickets, in order to determine whether the secure instruments are ripped, have a tear, have been tampered with, or have been exposed to a high amount of mechanical wear. It should be noted, however, that the present invention should not be limited to use with secure instruments. The present invention may be used to measure the porosity and/or the permeability of any desired object, material, or membrane. Further, embodiments of the present invention may also be used to detect tears in a substrate or material.

Figure 1:
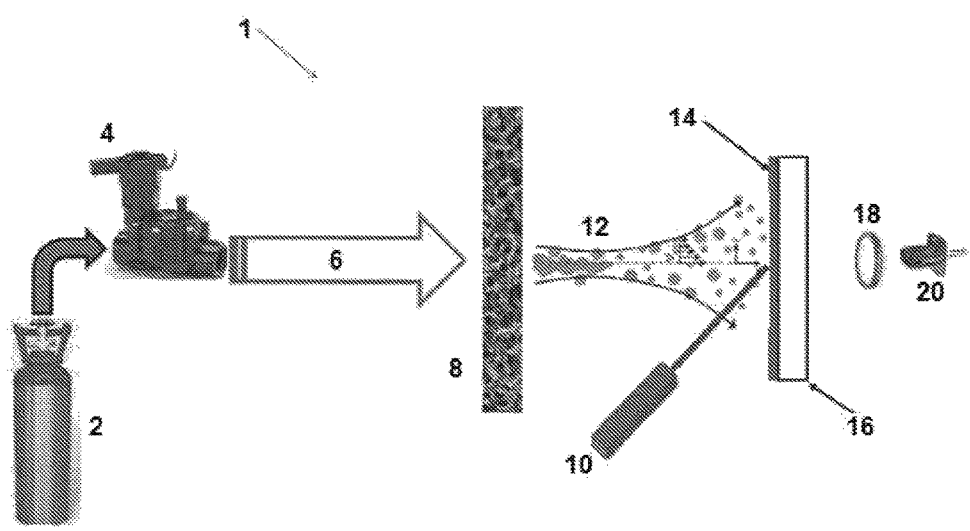
FIG. 1 is a diagram of an apparatus for testing the porosity or the permeability of an object, such as a banknote, according to an embodiment of the present disclosure.

FIG. 1 illustrates a diagram of an apparatus 1 for testing the porosity or the permeability of a secure instrument 8, according to an embodiment of the present disclosure. The apparatus 1 may include a fluid container 2 and a fluid dispenser or source 4. The fluid source 4 may be any device known to those skilled in the art that is configured to dispense, direct, and/or control the flow of a fluid (i.e., a liquid or a gas) including, but not limited to, a pump and a line gas source. In the embodiment of FIG. 1, for example, the fluid source 4 may be a valve. The fluid source 4 may be powered by any means known to those skilled in the art, including but not limited to, electric, hydraulic, motor, pneumatic, and manual. In addition, the fluid source 4 may include multiple fluid dispensing outlets. Alternatively, as illustrated in FIG. 1, the fluid source 4 may include a single dispensing outlet 6.

The fluid source 4 may be connected to a fluid container 2. The fluid container 2 may hold any fluid (i.e., liquid or gas) known to those skilled in the art that is capable of displacing an equilibrium concentration of oxygen in a gasochromic material 14 upon contact with the gasochromic material 14. For example, the fluid may be any liquid or gas that is rich in oxygen. Alternatively, the fluid may be any liquid or gas that contains substantially no oxygen, including, but not limited to argon, helium, xenon, and nitrogen.

As previously discussed, the fluid may be capable of displacing the equilibrium concentration of oxygen in the gasochromic material 14. The gasochromic material 14 may be any material configured to change the intensity or spectral position of its emission or absorption bands in response to various molecular moieties. For example, the gasochromic material 14 may be any desired low molecular weight polymer material known to those skilled in the art that contains gasochromic molecules. The gasochromic molecules may be any molecules configured to emit light under excitation by UV light or other wavelengths including, but not limited to, platinum, rhodium, Pt-porophyrines, and iridium containing phosphyrines and nano-crystaline zinc-oxide. For example, in one embodiment, the gasochromic material 14 may include a low molecular weight polymer coating, such as polystyrene (PS), containing gasochromic molecules. Alternatively, as illustrated in FIG. 1, the gasochromic material 14 may be a film, such as polystyrene, containing gasochromic molecules.

FIG. 1 further illustrates that the gasochromic material 14 may be mounted on a substrate 16. The substrate 16 may be any substrate configured to maintain the gasochromic material 14 in a desired position and configured to enable a detection device 20 to sense light emitted from the gasochromic material 14 when the fluid contacts the gasochromic material 14. In one embodiment, as illustrated in FIG. 1, the substrate 16 may be a transparent substrate. In alternative embodiments, the substrate 16 may be doped with gasochromic moieties.

As shown in FIG. 3, in an embodiment, the gasochromic material may be embedded in the substrate 16. For example, the gasochromic material 301 can be embedded throughout the thickness of the substrate 16. According to certain exemplary embodiments, the embedded gasochromic material can include gasochromic elements, such as particles, dissolved molecules, or security features, or can also include material embedded into the substrate 16 in the sizing material used in the manufacture of paper and/or the adhesives used to secure security threads inside the substrate 16. As described herein, the porosity or the permeability of the substrate is related to the output of the excited gasochromic material embedded in the substrate 16.

Embedding the gasochromic materials throughout the substrate 16 can further enable the porosity or the permeability of the substrate 16 to be tested from both sides of the substrate 16. Embedding the gasochromic materials throughout the substrate 16 can also enable high speed testing of the porosity or the permeability of the substrate 16. Moreover, changes in the porosity or permeability of the substrate can be determined based on the output of excited gasochromic elements embedded in the substrate 16.

Figure 6:
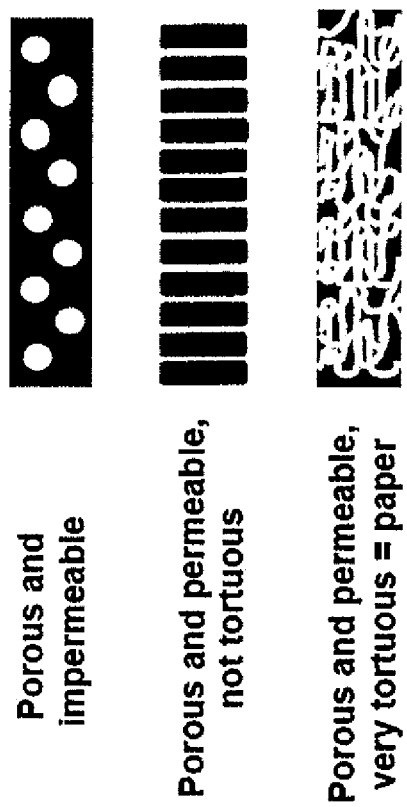
FIG. 6 shows the porosity and permeability of certain substrates.
Figure 7:
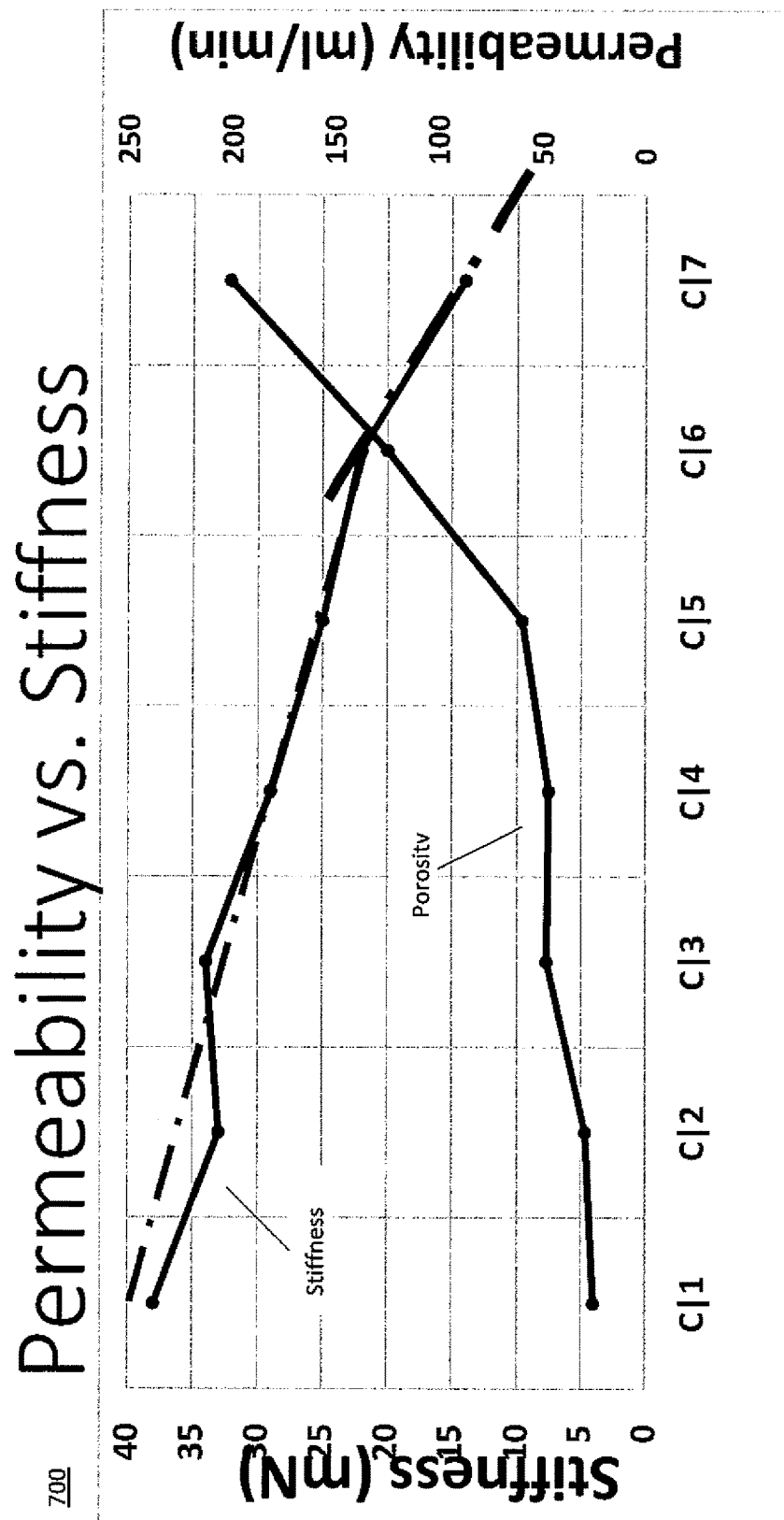
FIG. 7 is a graph comparing permeability to stiffness.
Figure 8:
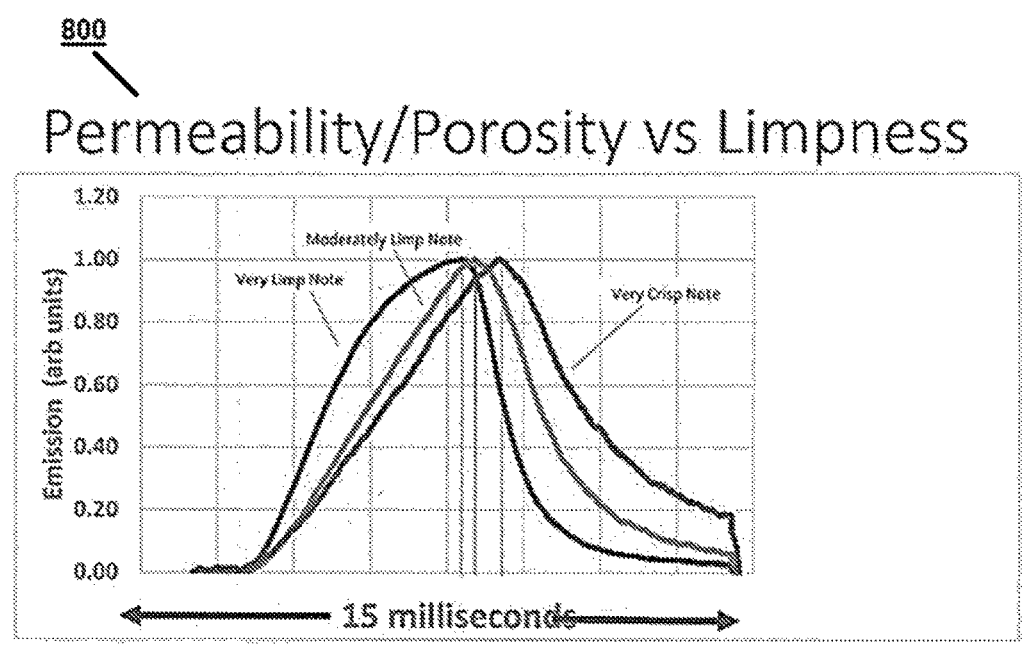
FIG. 8 is a graph comparing permeability to limpness.

Further, embedding the gasochromic elements in the substrate 16 may also enable detection of changes in the substrate 16, such as limpness. FIG. 6 shows the porosity and permeability of various substrates. For example, FIG. 6 shows examples of: (1) a porous and impermeable substrate; (2) a porous and permeable, not tortuous substrate; and (3) a porous and permeable, very tortuous substrate, which may be paper. Further, FIG. 7 shows a graph 700 comparing the stiffness of a substrate to the permeability/porosity of the substrate. FIG. 8 shows a graph 800 comparing the permeability/porosity to the limpness of a note, and shows the emission characteristics of three notes: (1) a very limp note; (2) a moderately limp note; and (3) a very crisp note.

As previously discussed, the gasochromic material 14 may be configured to emit light under excitation. FIG. 1 illustrates that excitation of the gasochromic material 14 may be accomplished via an excitation source 10. The excitation source 10 may be any device configured to emit light that is capable of causing the gasochromic molecules in the gasochromic material 14 to emit a phosphorescent transition from a triplet state to a singlet ground state. For example, the excitation source 10 may be an LED or a lamp. Alternatively, as illustrated in FIG. 1, the excitation source may be a laser.

When the gasochromic molecules in the gasochromic material 14 are in an excited state, the light emitted may be sensed by a detection device 20, which is part of the apparatus 1. The detection device 20 may be any device known to those skilled in the art that may be configured to sense light, capture images, and/or create images. In one embodiment, for example, the detection device 20 may include an imaging device, such as a camera. In addition, or alternatively, the detection device 20 may include at least one sensor (not shown) configured to sense the emitted light. The sensors may be any sensors known to those skilled in the art including, but not limited to, photodiodes, photomultipliers, and photovoltaic cells.

FIG. 1 further illustrates that the detection device 20 may include one or more filters 18. The filter 18 may be any device known to those skilled in the art configured to reject all light other than the light emitted from the gasochromic molecules. For example, in one embodiment, the filter may be a Schott red glass 610 (RG 610).

Figure 2:
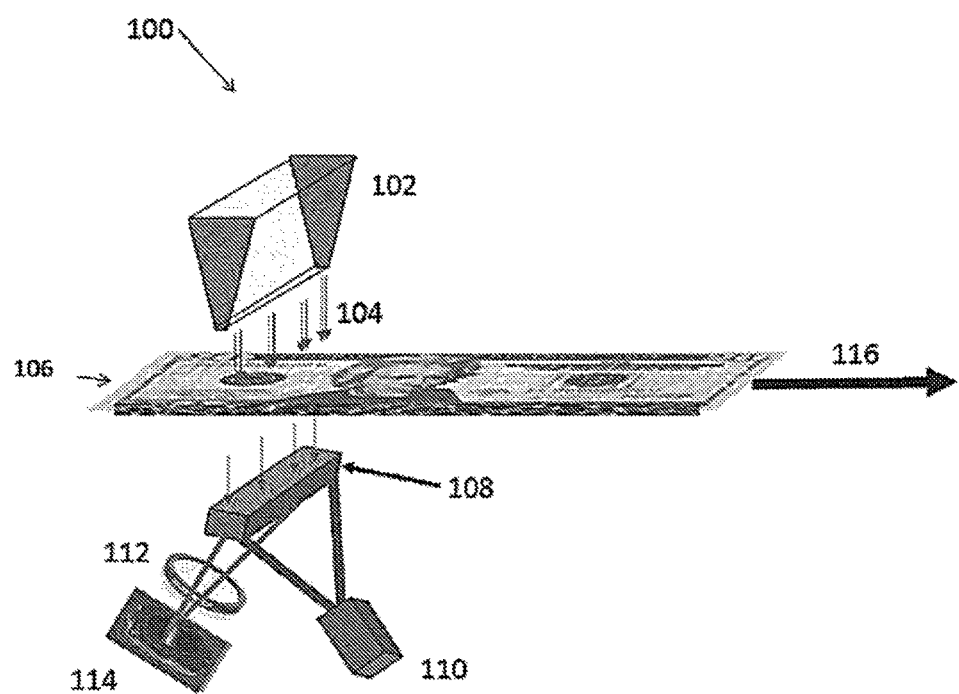
FIG. 2 is diagram of an apparatus for testing the porosity or the permeability of an object according to an embodiment of the present disclosure.

FIG. 2 illustrates a diagram of an apparatus 100 for testing the porosity or the permeability of a secure instrument 106 according to another embodiment of the present disclosure. The apparatus 100 of FIG. 2 may include features that are similar to the apparatus of FIG. 1. For example, the apparatus may include a fluid dispenser or source 102 configured to dispense a fluid (i.e., a liquid or a gas). The fluid source 102 may be any fluid source known to those skilled in the art that is configured to direct a flow of the fluid along a width of the secure instrument 106 as the secure instrument is advanced along its longitudinal axis 116. For example, as illustrated in FIG. 2, the fluid source 102 may be a line gas source. The fluid source 102 may further include any desired number of dispensing outlets 104 known to those skilled in the art. For example, as illustrated in FIG. 2, the fluid source 102 may contain a single dispensing outlet 104 extending along the length of the fluid source 102, and configured to extend along the width of the secure instrument 106.

Similar to FIG. 1, the fluid may be any liquid or gas configured to displace the equilibrium concentration of oxygen in a gasochromic material 108, such as a liquid or gas rich in oxygen or a liquid or gas containing substantially no oxygen. In the embodiment of FIG. 2, for example, the fluid may be a gas capable of being dispensed through the line gas source.

The apparatus 100 of FIG. 2 may further include a gasochromic material 108 mounted on a substrate that may be configured to enable a detection device 114 to sense light emitted from the gasochromic material 108 disposed on a transparent substrate. Like the gasochromic material 14 of FIG. 1, the gasochromic material of FIG. 2 may include a plurality of gasochromic molecules capable of emitting light upon receipt of light from an excitation source 110. The gasochromic material 108 may be any low molecular weight material, such as a film, that includes gasochromic molecules. The gasochromic material may be embedded in a substrate. Alternatively, the embodiment of FIG. 2 illustrates that the gasochromic material 108 may be a coating or may be a transparent substrate doped with gasochromic moieties.

The excitation source 110 of FIG. 2 may also be similar to the excitation source 10 of FIG. 1. For example, the excitation source 110 may be an LED, a lamp, or, as illustrated in FIG. 2, a laser. The excitation source 110 may further be configured to direct light along a single path. Alternatively, the excitation source 110 may be configured to emit light along any desired number of optical pathways known to those skilled in the art. For example, as illustrated in FIG. 2, the excitation source 110 may be configured to emit light along at least two pathways.

The apparatus 100 of FIG. 2 further includes a detection device 114. Like the detection device 20 of FIG. 1, the detection device 114 of FIG. 2 may include at least one filter 112 configured to reject all light other than the light emitted from the gasochromic molecules in the gasochromic material 108. In addition, the detection device 114 may include any device known to those skilled in the art that may be configured to sense light, capture images, and/or create images. The detection device 114 may also include at least one sensor (not shown) configured to sense or detect the emitted light. The sensors may be any sensors known to those skilled in the art including, but not limited to, photodiodes, photomultipliers, and photovoltaic cells. For example, in the embodiment of FIG. 2, the detection device 114 may be a line scan camera. In addition, as illustrated in FIG. 2, the detection device 114 may be configured to obtain a plurality of images of the light emitted from the gasochromic molecules as the secure instrument 106 is advanced through a space between the fluid source 102 and the gasochromic material 108 along the longitudinal axis 116 of the secure instrument 106.

Figure 4A:
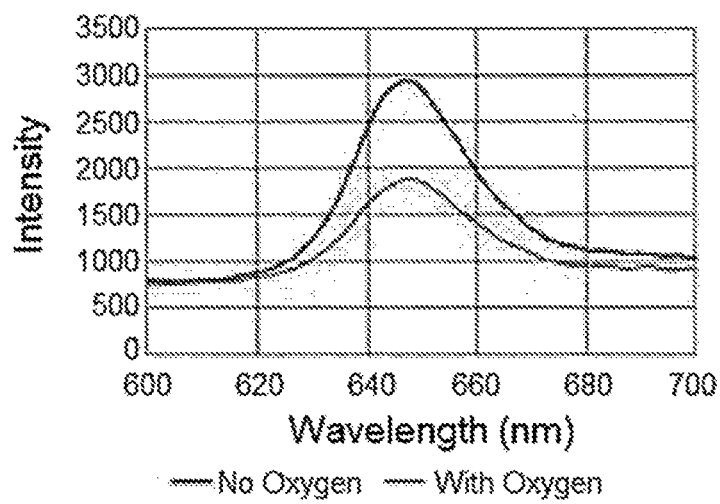
FIGS. 4A and 4B are graphs comparing the emission of gasochromic molecules in response to contact with a fluid rich in oxygen and a fluid containing substantially no oxygen.
Figure 4B:
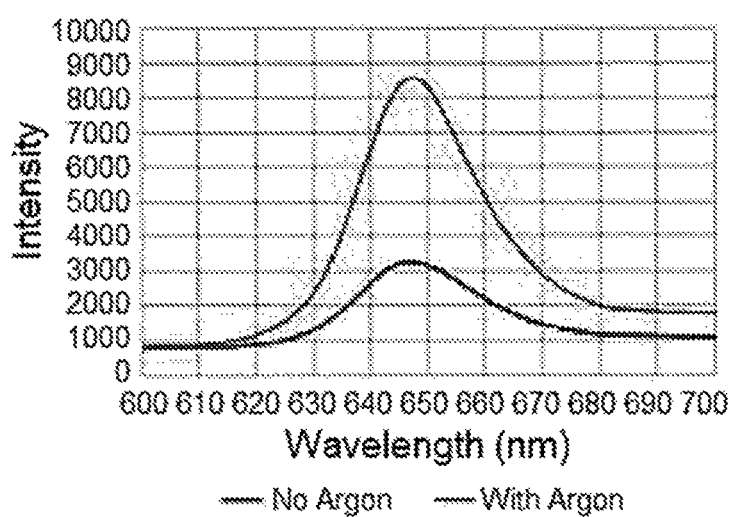

The apparatus 1 of FIG. 1 and the apparatus 100 of FIG. 2 may also each include a processor (not show) known to those skilled in the art. The processor may be configured to receive the detected images from the detection devices and output porosity or the permeability data based on the detected images. The porosity or the permeability data may include data corresponding to the light emitted from the gasochromic molecules in the gasochromic material 14, 108. For example, as illustrated in FIG. 4A, when a fluid that is rich in oxygen is dispensed to flow through the secure instrument 8, 106, the light that is emitted from the gasochromic material is inversely related to the porosity of the material: a lower detection of emitted light corresponds to a higher level of porosity. Conversely, as illustrated in FIG. 4B, when a fluid that has substantially no oxygen is dispensed to flow through the secure instrument 8, 106, the detected emitted light is directly related to the porosity of the material: a lower detection of emitted light corresponds to a lower level of porosity.

Figure 5B:
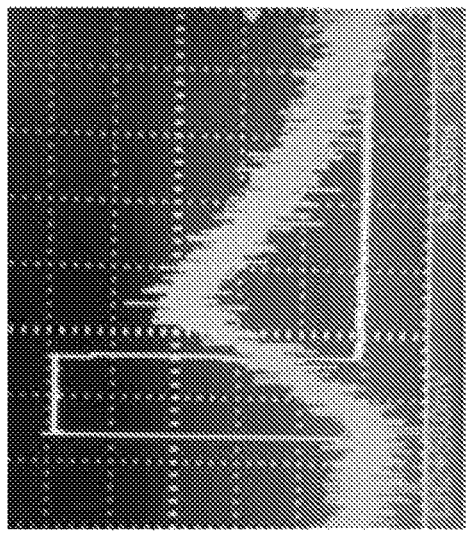
FIGS. 5A and 5B are graphs comparing the porosity of an uncirculated banknote and a circulated banknote.
Figure 5A:
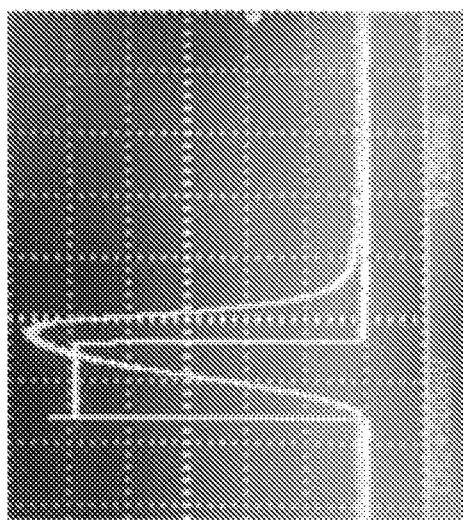

FIGS. 5A and 5B illustrate porosity data of a circulated banknote (FIG. 5A) and an uncirculated banknote (FIG. 5B) that have been tested using the apparatus of FIG. 1 with fluid containing substantially no oxygen. Typically, uncirculated banknotes have a lower porosity than circulated banknotes, because the uncirculated banknotes have not been exposed to mechanical wear. The porosity data shown in FIGS. 5A and 5B is consistent with this fact. As illustrated in FIGS. 5A and 5B, the porosity test of the circulated banknote (FIG. 5A) detected more emitted light from the gasochromic material than the porosity test of the uncirculated banknote (FIG. 5B).

Referring back to FIGS. 1 and 2, the present disclosure includes a method of testing the porosity or the permeability of an object, material, or membrane. The method may first include positioning the object, material, or membrane in a space between the fluid source 4, 102 and the gasochromic material 14, 108. In the embodiment of FIG. 1, the object, material, or membrane may be positioned such that it may be secured between the fluid source 4 and the gasochromic material 14. For example, apparatus 1 may include a device configured to maintain the material or membrane in a substantially flat position, such as a plate (not shown). The device (i.e., plate) may also be configured to attach to the fluid source 4 and enable the fluid source 4 to dispense the fluid through the material or membrane.

Alternatively, as illustrated in FIG. 2, the object, material, or membrane may be positioned such that the object, material, or membrane may be advanced along its longitudinal axis 116, and thereby movable relative to the fluid source 102, the gasochromic material 108, and the detection device 114.

Figure 10:
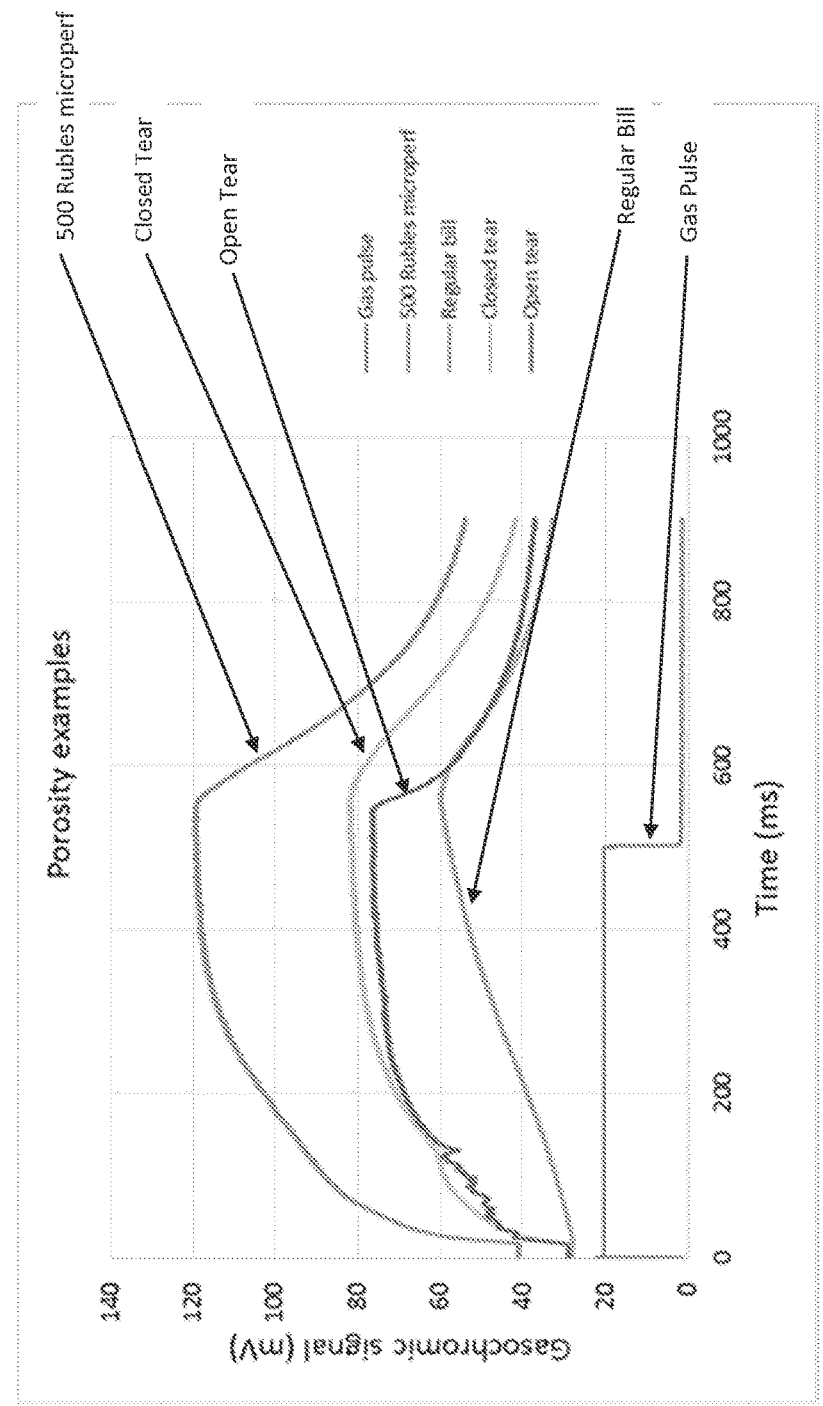
FIG. 10 is a graph comparing the gasochromic signal response related to several specimens.

As previously noted, the exemplary methods may also be used to detect a tear in a substrate or material. A tear may include an open or closed tear. For example, an open tear may include, e.g., a hole, a perforation, or a rip, or any other discontinuity in the substrate or material where there is substrate or material missing. A closed tear may include, for example, a discontinuity in the substrate or material such as a rip where the substrate or material is still present and therefore makes the tear more difficult to detect. FIG. 10 is a graph showing gasochromic signal response to certain materials. As shown in FIG. 10, the exemplary gasochromic signal response to an open tear and a closed tear are different and are distinguishable from each other and the other materials shown in FIG. 10.

As previously discussed, the object, material, or membrane may be any sample where porosity testing is desired. Samples may be used from a variety of fields including, but not limited to, pharmaceuticals, ceramics, metallurgy, materials, manufacturing, earth sciences, soils mechanics, and engineering. The embodiments of FIGS. 1 and 2 illustrate that the object, material, or membrane sample may in the form of a secure instrument 8, 106. The secure instrument 8, 106 may be a banknote having a substrate, visual data, and a security feature. The banknote may be any banknote from any country, including but not limited to, banknotes from the United States, China, Europe, Russia, Canada and India.

Figure 9:
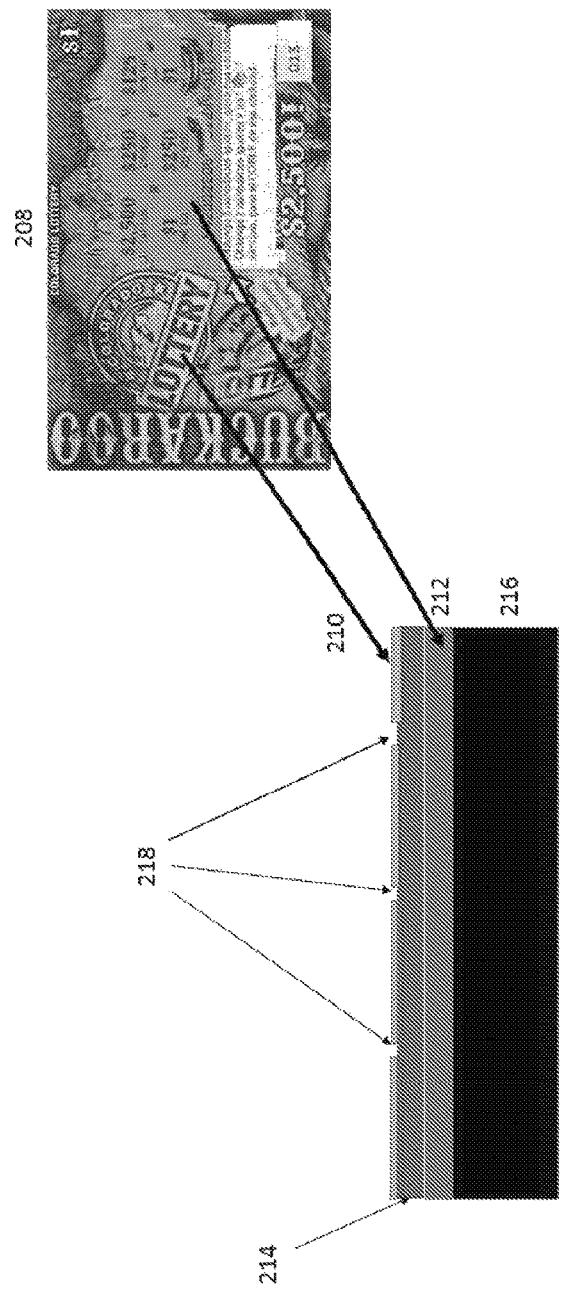
FIG. 9 is a diagram of a lottery scratch ticket according to an embodiment of the present disclosure.

FIGS. 1 and 2 illustrate a sample where it is desired to obtain characteristics about the porosity of the entire sample. Alternatively, as illustrated in FIG. 9, the object, material, or membrane may be a sample including multiple layers, such that porosity of one of the layers may be obtained. For example, FIG. 9 illustrates that the object may be a lottery scratch ticket 208 that includes a scratch layer 210 and printed data layer 212. The printed data 212 may be covered by the scratch layer 210. Because lottery scratch tickets are subject to tampering, it may be desirable to obtain characteristics about the porosity or permeability of the scratch layer 210. For example, it may be necessary to determine whether there are pinpricks 218 in the scratch layer 210 that provide access to the printed data 212.

In order to obtain porosity and permeability data corresponding to the scratch layer 210, FIG. 9 illustrates that a layer of gasochromic material 214 may be located on the lottery scratch ticket 208 between the scratch layer 210 and the printed data 212. Like the embodiments of FIGS. 1 and 2, the gasochromic material 214 may be any low molecular weight material, such as a film or coating that includes gasochromic molecules. The gasochromic material 214 may further be a transparent material such that the printed data 212 may be visually accessed upon removal of the scratch layer 210. Alternatively, or in addition, the gasochromic material 214 may be configured to be removed with the scratch layer 210 when the scratch layer 210 is subject to scratching, scraping, or the like.

FIG. 9 further illustrates that the lottery scratch ticket 208 may be mounted on a substrate 216. Like the embodiments of FIGS. 1 and 2, the substrate 216 may be a transparent substrate. To determine the porosity of the scratch layer 210, the embodiment of FIG. 9 may be used in conjunction with the fluid sources 4, 102, excitation sources 10, 110, filters 18, 112, and detection devices 20, 114 of FIGS. 1 and 2. The scratch layer 210 may be any material known to those skilled in the art and configured to be removed upon scratching, scraping, or the like. In addition, the scratch layer 210 may be any material configured to allow penetration of light from the excitation sources 10, 110 and emissions from the excited gasochromic molecules in the gasochromic material 214.

Returning to FIGS. 1 and 2, after the object, material, or membrane is positioned in the space between the fluid source 4, 102 and the gasochromic material 14, 108, fluid may be dispensed through the outlets 6, 104 of the fluid source 4, 102 such that at least a portion of the dispensed fluid 12 can flow through the object, material, or membrane. As illustrated in FIGS. 1 and 2, fluid that flows completely through the object, material, or membrane may contact the gasochromic material 14, 108 and may quench light emission of the gasochromic molecules in the gasochromic material 14, 108. In particular, FIG. 1 illustrates that the portion of the dispensed fluid 12 that flows from a side of the secure instrument 8 facing the fluid source 4 to a side of the secure instrument 8 facing the gasochromic material 14 may disperse along a width of the gasochromic material 14. For example, as illustrated in FIG. 1, at least some of the portion of the dispensed fluid 12 may disperse in a direction substantially perpendicular to a flow path of the fluid through the secure instrument 8.

The method further includes powering the excitation source 10, 110, such that the excitation source 10, 110 may emit UV or other wavelengths configured to excite the gasochromic molecules in the gasochromic material 14, 108. The excitation source 10, 110 may be positioned such that at least one path of light from the excitation source intersects with the gasochromic material 14, 108. In addition, the excitation source 10, 110 may be powered prior to, during, and after the fluid contacts the gasochromic material 14, 108, so that the detection device may be capable of detecting emitted light corresponding to the equilibrium concentration of oxygen in the gasochromic material 14, 108, and emitted light corresponding to the displaced equilibrium concentration of oxygen in the gasochromic material 14, 108. Thus, the porosity of the object, material, or membrane is related to the change in the detected emitted light corresponding to the equilibrium concentration of oxygen in the gasochromic material 14, 108 and the detected emitted light corresponding to the displaced equilibrium concentration of oxygen in the gasochromic material 14, 108.

During excitation of the gasochromic molecules in the gasochromic material 14, 108, the detection device 20, 114 may be detecting the emitted light by first, using the filter 18, 112 to reject all light other than the light emitted from the gasochromic molecules. After filtering the light, the detection device 20, 114 may use the sensors therein to detect the emitted light. The detection device 20, 114 may further transmit the detected light signals to the processor (not shown), which may be configured to determine and output data corresponding to the porosity and permeability and thereby the fitness (e.g., mechanical wear, rips, pinpricks, and tears) of the object, material, or membrane used in conjunction with the apparatus 1, 100 by analyzing the information received from the detection device 20, 114.

The determination and output of data corresponding to the porosity and permeability of the object, material or membrane may be calculated based on an average porosity and permeability over the entire material or membrane. For example, in the embodiment of FIG. 1, the secure instrument 8 may be secured between the fluid source 4 and the gasochromic material 14; and the fluid source 4 may be configured to dispense the fluid on the secure instrument 8 such that a porosity determination may be made across the entire note.

Alternatively, porosity may be determined along the length of the banknote 106. As illustrated in FIG. 2, the secure instrument 106 may be positioned in a space between the fluid source 102 and the gasochromic material 108. The secure instrument 106 may be advanced through the space along its longitudinal axis 116. As the secure instrument 106 is advanced through the space, the fluid source 102 may dispense fluid along the length of the secure instrument 106, such that the detection device 114 may obtain data corresponding to the porosity of the secure instrument 106 along its length.

The embodiments and examples above are illustrative, and many variations can be introduced to them without departing from the spirit of the disclosure or from the scope of the invention. For example, elements and/or features of different illustrative and exemplary embodiments herein may be combined with each other and/or substituted with each other within the scope of this disclosure. For a better understanding of the invention, its operating advantages and the specific objects attained by its uses, reference should be had to the accompanying drawings and descriptive matter in which there is illustrated a preferred embodiment of the invention.

What is claimed is:

1. A method of evaluating the fitness of an object based on determination of a measure of permeability of the object, comprising:
   positioning the object between a fluid source and a gasochromic material;
   dispensing a fluid from the fluid source towards the object such that at least a portion of the fluid flows through the object and contacts the gasochromic material;
   exciting the gasochromic material with an excitation source directed toward the gasochromic material such that an emission of the gasochromic material is in response to the excitation source and the fluid, wherein the excitation source is not directed toward the object;
   detecting the emission from the gasochromic material to determine the permeability of the object; and
   evaluating the fitness of the object based on the determination of the permeability of the object.

2. The method of claim 1 wherein evaluating the fitness of the object is determining presence of a tear in the object, determining limpness of the object or determining mechanical wear of the object.

3. The method of claim 1 wherein the fluid is a gas rich in oxygen or containing substantially no oxygen.

4. The method of claim 1 wherein the gasochromic material is coated on a substrate.

5. The method of claim 1 wherein the object is a secure instrument including a substrate, visual data, and a security feature.

6. The method of claim 5 wherein the secure instrument is a banknote.

7. The method of claim 1 wherein the object is a lottery scratch ticket comprising a scratch layer and a printed data layer.

8. The method of claim 1 further comprising advancing the object through a space between the fluid source and the gasochromic material.

9. An apparatus for evaluating the fitness of an object based on a determination of a measure of permeability of the object, comprising:
   a gasochromic material;
   a fluid source for dispensing fluid towards the object disposed between the fluid source and the gasochromic material;
   an excitation source directed toward the gasochromic material for exciting the gasochromic material such that an emission of the gasochromic material is in response to the excitation source and the fluid, wherein the excitation source is not directed toward the object; and
   a detection device for detecting the emission of the gasochromic material to determine the permeability of the object for evaluating the fitness of the object.

10. The apparatus of claim 9 wherein the fluid is a gas rich in oxygen or containing substantially no oxygen.

11. The apparatus of claim 9 wherein the gasochromic material is coated on a substrate.

12. The apparatus of claim 9 wherein the object is a secure instrument including a substrate, visual data, and a security feature.

13. The apparatus of claim 12 wherein the secure instrument is a banknote.

14. The apparatus of claim 9 wherein the object is a lottery scratch ticket comprising a scratch layer and a printed data layer.

15. The apparatus of claim 9 further comprising a transport device for advancing the object through a space between the fluid source and the gasochromic material.

16. The apparatus of claim 9 wherein the excitation source is a light emitting diode, a laser or a lamp.

17. The apparatus of claim 9 wherein the detection device includes photodiodes, photomultipliers or photovoltaic cells.

* * * * *